United States Patent [19]

Carli

[11] Patent Number: 4,632,828
[45] Date of Patent: Dec. 30, 1986

[54] PHARMACEUTICAL COMPOSITION

[75] Inventor: Fabio Carli, Turin, Italy

[73] Assignee: Farmitalia Carlo Erba S.p.A., Milan, Italy

[21] Appl. No.: 698,784

[22] Filed: Feb. 6, 1985

[30] Foreign Application Priority Data

Feb. 8, 1984 [GB] United Kingdom ............... 8403360

[51] Int. Cl.$^4$ ............................................. A61K 31/56
[52] U.S. Cl. ....................................... 424/80; 514/178
[58] Field of Search ........................... 514/178; 424/80

[56] References Cited

U.S. PATENT DOCUMENTS 4,038,389 7/1977 Lamb ................................. 514/178
4,482,534 11/1984 Blank ................................. 424/80

FOREIGN PATENT DOCUMENTS 1380171 1/1975 United Kingdom ................. 424/80

Primary Examiner—Elbert L. Roberts
Attorney, Agent, or Firm—Oblon, Fisher, Spivak, McClelland & Maier

[57] ABSTRACT

A water-swellable, water-insoluble polymer is loaded with methylhydroxyprogesterone acetate (MAP) by:
(a) preparing and grinding a mixture of a said polymer and MAP; or
(b)(i) preparing a mixture of a said polymer which is stable under the heating to which the mixture is subjected in step (ii) and MAP and (ii) heating the mixture up to the melting temperature of MAP; or
(c) swelling a said polymer with a MAP solution capable thereof and drying the resulting swollen polymer/MAP system.

The MAP loaded polymer is useful as a pharmaceutical composition.

14 Claims, No Drawings

PHARMACEUTICAL COMPOSITION

BACKGROUND OF THE INVENTION

1. Field of the Invention

The present invention relates to formulations of 6α-methyl, 17α-hydroxy-progesterone acetate (medroxyprogesterone acetate or MAP).

2. Description of the Prior Art

MAP was independently synthesized in 1958 by two different research groups. It is a synthetic steroid derived from progesterone and exerts, by oral and intramuscular routes, a progestinic activity.

MAP is also used, at higher doses and by the same administration routes, in cancer treatment. In this therapeutic application however, the oral treatment requires very high doses because of the poor bioavailability of the active drug substance. This characteristic is related to the poor wettability and dissolution of the compound in aqueous and biological media. These properties of the compound control and limit the overall absorptability of the compound.

The wettability and dissolution properties of an active drug substance greatly influence its bioavailability; in many cases very active drugs present a poor absorption profile because of their unfavourable dissolution characteristics.

Usually the reduction of the particle size of the drug and the addition of wetting agents have been factors which have been utilized to overcome these problems, but very frequently they prove to be not effective enough. Therefore much effort has been devoted to develop new formulations or new techniques to achieve improved results.

Considerable research effort has recently opened two new research lines based on the preparation of "solid dispersions" and of "inclusion compounds". In the former approach the drug is molecularly dispersed in the carrier, usually a water-soluble polymer (S. Riegelman, W. L. Chiou No. 987,588 4/1976 Canada), while in the latter approach the drug forms molecular complexes with water-soluble cyclodextrins (J. Szejtli, "Cyclodextrins and their inclusion compounds", Akademia Viado, Budapest 1982). A need therefore continues to exist for an improved form of MAP which increases its bioavailability.

SUMMARY OF THE INVENTION

Accordingly, one object of the present invention is to provide a MAP containing formulation which increases the bioavailability of MAP in subjects administered the compound.

Briefly, this object and other objects of the present invention as hereinafter will become more readily apparent can be attained by a process, which provides a methylhydroxyprogesterone acetate containing composition exhibiting outstanding bioavailability characteristics, comprising:

(a) preparing and grinding a mixture of a waterswellable, water-insoluble polymer and MAP; or (b)(i) preparing a mixture of a said polymer which is stable under the heating to which the mixture is subjected in step (ii) and MAP and (ii) heating the mixture up to the melting temperature of MAP; or (c) swelling said polymer with a MAP solution capable of swelling the polymer and drying the resulting swollen polymer/MAP system.

DETAILED DESCRIPTION OF THE PREFERRED EMBODIMENTS

The present invention involves systems in which MAP is loaded in and on any swellable, water-insoluble polymer (or combination thereof), such as for instance, cross-linked polyvinylpyrrolidone, hereinafter referred to as cross-linked PVP, (National Formulary XV, Supplement 3, p. 368), cross-linked sodium carboxymethylcellulose (National Formulary XV, Supplement 3, p. 367), cross-linked dextran, and the like by using three different preparation techniques.

The MAP in and on the swellable, water-insoluble polymer formulation of the invention greatly enhances the dissolution and wettability properties of MAP in aqueous or biological media because of one or both of the following factors:

(1) Reduction of the dissolution energy of MAP brought about by its complete or partial amorphization or by the transition of its original crystalline state into a higher energy state (lower melting point).

(2) Increase of the wettability of MAP by dispersing its molecules in and on the network of a highly hydrophilic and swellable polymer.

The present invention accordingly provides a process for loading a water-swellable, water-insoluble polymer with methylhydroxyprogesterone acetate (MAP).

Important advantages of systems which consist of drugs loaded in and on hydrophilic, swellable, water-insoluble polymers over "solid dispersions" and "inclusion compounds" are:

1. Greater increases of drug wettability because of the greater hydrophilicity and swelling capacity in water of the hydrophilic, swellable, water-insoluble polymers.

2. More rapid disintegration in water of the system and faster dispersion of the drug particles. Some of the hydrophilic, swellable, water-insoluble polymers which may be used in the present process are, in fact, already used and marketed as disintegrants for oral solid dosage forms.

3. Avoidance of the viscous layer around the drug which can be associated with the use of water-soluble polymers and can hinder the drug diffusion and slow down the dissolution process.

The MAP polymer system of the invention consists of MAP and at least one hydrophilic, swellable, water-insoluble polymer. Suitable examples of such polymers include cross-linked PVP, cross-linked sodium carboxymethylcellulose, cross-linked starch, cross-linked dextran, and the like, said polymers having the following common characteristics:

1. High swelling ability in water (from 0.1 ml to 100 ml of water volume uptake per gram of dry polymer). This characteristic brings about a high degree of swelling and effective disintegration (in water or in biological fluids) of the system with a powerful dispersion of its constituents and an immediate release of MAP molecules.

2. A fast rate of water swelling. For example, cross-linked PVP achieves maximum swelling in less than live minutes. This property allows the swelling, disintegration, dispersion and dissolution of the MAP molecules in a very short period of time.

3. Water insolubility. This property rules out possible negative effects which are able to slow down the MAP dissolution process, for instance, the building up of a viscous layer around MAP, and brings about the formation of a finely dispersed homogeneous suspension which assures a rapid gastric emptying to the absorption site.

Three methods can be utilized to prepare a formulation composed of MAP and at least one of the insoluble swellable polymers mentioned supra. (1) One method is to grind a mixture of MAP and the polymer. (2) A second method is to heat a mixture of MAP and the polymer up to the melting temperature of MAP. (3) A third method is to swell the polymer with a solution of MAP, and then dry the swollen, MAP impregnated polymer. The details of the three methods are given below.

1. The cogrinding of a mixture of MAP and the polymer:

A dry mixture of MAP and at least one of the swellable insoluble polymers mentioned supra is placed in a rotating ball mill, in a vibrational ball mill, in an automatic mortar mill or any other suitable crushing apparatus, and is ground until complete amorphization of the crystalline MAP is achieved. The completeness of the amorphization process can be checked by the absence in the Differential Scanning Calorimetry thermogram of the resulting drug-polymer system of the transition peak indicative of the solid/liquid endothermic transition of crystalline MAP. That is, the enthalpy of melting is practically null. The grinding of the MAP-swellable polymer mixture can also be stopped at any time over the range of amorphization of 0–100% of MAP, as measured by the reduction of the enthalpy of melting of the crystalline MAP, which is a level of amorphization which is sufficient to sensibly increase the MAP dissolution rate. Alternatively, the grinding of the MAP-swellable polymer mixture can be stopped at any time the original crystalline form of MAP has been transformed into another, more energetic form. This transformation is indicated by the shifting of the original endothermic peak in the DSC thermogram to lower temperatures. This new, higher energy form of MAP provides MAP in a form in which MAP exhibits a higher dissolution rate and bioavailability.

The weight ratios between MAP and the swellable water-insoluble polymer in the mixture to be ground can vary from 1:0.1 to 1:100 w/w. The MAP:polymer ratio preferably is from 1:1 to 1:100 w/w MAP:polymer. For each quantity of mixture the correct time of grinding necessary to achieve the desired degree of amorphization or the formation of a higher energy form of MAP must be checked. Therefore, for each MAP-polymer system the most practical combination of weight ratio and time of grinding can be identified. Suitable examples of drug: swellable insoluble polymer weight ratios and grinding times will be given later.

The ground mixture of MAP and the swellable polymer can then be forced through a sieve to eliminate possible aggregates and subsequently can be mixed in any mixing device to guarantee further homogeneity.

The resulting powdered ground system of MAP and swellable polymer can be used to prepare any desired solid dosage form, e.g. capsules, tablets, and the like, with or without the addition of any of the common excipients used in pharmaceutical formulations.

2. Heating of a mixture of the drug and the polymer up to melting temperature of MAP.

A dry mixture of crystalline MAP and any of the swellable insoluble polymers mentioned supra which have a good thermal stability at the melting point of MAP is placed in a container inside a thermoregulated high vacuum oven. After evacuation, a nitrogen flow is established over the MAP-polymer mixture, and the temperature is raised to a value sufficient to bring about the melting of MAP. Alternatively, the mixture of MAP and the polymer is placed in the glass flask of a rotating evaporator. After evacuation, a flow of nitrogen is established over the MAP-polymer mixture and the glass flask placed in an oil bath at a temperature sufficient to bring about the melting of MAP. Any other heating apparatus such as a hot plate, muffle, tube oven, or the like can be usefully applied, as long as the temperature can be carefully checked and held constant.

The MAP-polymer mixture is heated as long as the desired degree of amorphization (0–100%) of crystalline MAP is achieved, which can be checked by Differential Scanning Calorimetry.

Weight ratios of MAP and the polymer in the mixture to be heated can vary from 1:0.1 to 1:100 w/w MAP:polymer, preferably from 1:1 to 1:100 w/w MAP:polymer. For each MAP:polymer weight ratio composition and for each total amount of mixture, the time of heating necessary to achieve the desired degree of amorphization must be checked. Examples of MAP:polymer weight ratio compostions, of heating temperature and time will be given later.

The resulting heated mixture of MAP and swellable polymer can then be forced through a sieve to eliminate possible aggregates and subsequently mixed in any mixing device to guarantee further homogeneity. The resulting powdered MAP-polymer mixture can be used to prepare any desired solid dosage form such as tablet, capsule, or the like, with or without the addition of any of the common excipients used in pharmaceutical formulations.

3. Swelling of the polymer with a solution of MAP and subsequent drying.

A solution of MAP of desired concentration in any of the common solvents for MAP, such as methylenechloride, chloroform, acetone, and the like is prepared and subsequently poured over a predetermined amount of any one or combination thereof of the water-insoluble swellable polymers aforementioned. The resulting swollen powder is subsequently dried with any convenient apparatus. The volume of MAP solution which can be loaded on the chosen weight of polymer should be of any value up to the maximum swelling volume of the polymer in that particular solvent. The process of swelling can be carried out with any suitable apparatus. For example, one can add the correct volume of MAP solution to the chosen quantity of swellable insoluble polymer in a mortar, mix thoroughly and subsequently dry the resulting swollen powder in a vacuum oven, or one can place the desired quantity of swellable insoluble polymer in the glass flask of a rotating evaporater, add the correct volume of MAP solution and heat the resulting swollen polymer until it becomes dry.

The weight ratios between MAP and the polymer which can be obtained by the swelling method can vary from 1:0.1 to 1:100 w/w MAP:polymer, preferably from 1:1 to 1:100 w/w MAP:polymer. For each given solvent-polymer system the maximum amount of MAP which can be loaded in the polymer is limited by the solubility of MAP in that solvent and by the swelling volume of the polymer in that solvent. In any case, for each solvent-polymer system, by varying the quantity of MAP loaded, one can achieve a degree of amorphization (0–100%) of MAP sufficient to sensibly increase the dissolution rate or the transformation into a higher energy form. Examples of MAP:polymer weight ratio composition, of MAP solution volumes and of polymer weight will be given later on.

The MAP-polymer mixture resulting from the swelling and drying process can then be forced through a sieve to eliminate possible aggregates and subsequently mixed in any mixing device to guarantee further homogeneity. The resulting powdered MAP-polymer mixture can be used to prepare any desired solid dosage form such as tablet, capsules, and the like with or without the addition of any of the common excipients used in pharmaceutical formulations.

The amount of the MAP/polymer system of the invention which is administered to a subject will depend upon a variety of factors including the condition of the subject being treated and the age and condition of the patient.

Having generally described the invention, a further understanding can be obtained by reference to certain specific examples which are provided herein for purposes of illustration only and are not intended to be limiting unless otherwise specified.

EXAMPLE 1

A 2 gram amount of crystalline MAP and 6 gram of cross-linked PVP were mixed with a suitable mixer, subsequently placed in an automatic mortar mill and ground for 3 hours. The resulting MAP/cross-linked PVP system was then sieved to the 260 μm range and subsequently mixed with a suitable mixer. This powdered MAP/cross-linked PVP system could then be incorporated in any desired solid dosage form.

EXAMPLE 2

The MAP/cross-linked PVP system described in Example 1 has been employed to prepare tablets having the following unitary composition:
MAP/cross-linked PVP ground system: 200 mg
Cross-linked PVP: 40 mg
in which pure cross-linked PVP is added only as a disintegrating agent. These ingredients were thoroughly mixed with a suitable mixer and subsequently compressed to tablets with a 13 mm flat punch compaction machine.

EXAMPLE 3

The MAP/cross-linked PVP powdered system described in Example 1 has been employed to prepare capsules having the unitary composition as follows:
MAP/cross-linked PVP ground system: 200.0 mg
Cross-linked PVP: 40.0 mg
Magnesium stearate: 2.5 mg

EXAMPLE 4

A 0.7 gram amount of crystalline MAP and 3.5 gram of cross-linked sodium carboxymethylcellulose were mixed with a suitable mixer, subsequently placed in an automatic mortar mill and ground for 3 hours. The resulting MAP/cross-linked sodium carboxymethylcellulose powdered system was then sieved to 260 μm and subsequently mixed in a suitable mixer. This powdered MAP/cross-linked sodium carboxymethylcellulose system could then be made into any desired solid dosage form.

EXAMPLE 5

A 0.2 gram amount of crystalline MAP and 1.0 gram of cross-linked PVP were mixed with a suitable mixer, subsequently placed in the glass flask of a rotating evaporator, and heated in an oil bath at 215° C. for 45 minutes under a nitrogen flow. The resulting MAP/cross-linked PVP system was then sieved to 260 μm and mixed in a suitable mixer. This powdered system could then be made into any desired solid dosage form.

EXAMPLE 6

The MAP/cross-linked PVP system described in Example 5 has been employed to prepare tablets having the following unitary composition:
MAP/cross-linked PVP heated system: 300 mg
Cross-linked PVP: 60 mg
in which pure cross-linked PVP is added only as a disintegrating agent. The aforementioned ingredients were thoroughly mixed in a suitable mixer and subsequently compressed to tablets with a 13 mm flat punch compaction machine.

EXAMPLE 7

A 5 gram amount of crystalline MAP was dissolved in 100 ml methylenechloride. A 20 ml amount of this solution were poured over 5 gram of cross-linked PVP under gentle mixing in a mortar. The resulting swollen MAP/cross-linked PVP system was then dried in a vacuum oven at 60° C. for 2 hours. The dried powder obtained was then sieved to 260 μm and subsequently mixed in a suitable mixer. This powdered system could then be made into any desired solid dosage form.

EXAMPLE 8

The MAP/cross-linked PVP system described in Example 7 has been employed to prepare, by means of a 13 mm flat punch compaction machine, tablets having the following unitary composition:
MAP/cross-linked PVP (swelling system): 300 mg

EXAMPLE 9

The MAP/cross-linked PVP powdered system described in Example 7 has been employed to prepare tablets having the following composition:
MAP/cross-linked PVP (swelling system): 600 mg
Microcrystalline cellulose pH-101: 150 mg
Magnesium stearate: 6 mg

"IN VITRO" CHARACTERISTICS OF MAPSWELLABLE POLYMER SYSTEMS

1. Differential Scanning Calorimetry Data

The D.S.C. (T.A. 3000, Mettler) data relative to the formulations prepared by grinding described in Examples 1 and 4 are shown in Table I. By comparing these data with the D.S.C. analysis of the pure MAP and of the micronized pure MAP, it is possible to observe that in the case of the ground mixture (1:3 w/w) of MAP and cross-linked PVP, at three hours of grinding there is a 60% reduction of the original heat of fusion and the shifting of the original melting point (205.6° C.) to a lower value (196° C.). In the case of the ground mixture (1:5 w/w) of MAP and cross-linked sodium carboxymethylcellulose, after 3 hours of grinding there is a 50% degree of amorphization. The D.S.C. data of the MAP/swellable polymer system (Example 5) made by heating are also shown in Table I. There is a practically complete amorphization of MAP.

In the case of the MAP system prepared by swelling the cross-linked PVP with a solution of MAP in methylenechloride (Example 8) there is no reduction of heat of fusion, but a lowering of the original melting point.

2. Solubility Data

The solubility (saturation concentration) of the MAP/swellable polymer systems was measured by placing an excess amount of the powdered systems, equivalent to 50 mg of MAP, in flasks containing 50 ml of pH 5.5 buffer solution, at 37° C. The flasks were placed in a shaking thermostated apparatus and aliquots of sample solutions were taken by filtering through a Millipore membrane. The concentration of MAP in the filtered aliquot was determined both by spectrophotometry (SP8-100, Pye Unicam), after dilution with methanol, and by HPLC (column: Spherisorb S30DS2, Phase Sep.; mobile phase: acetonitrile/water 70/30 v/v; flow rate: 1 ml/min; U.V. detection, $\lambda=242$ nm), after dilution with acetonitrile. As shown in Table II, a relevant increase of the MAP solubility values is achieved, also at very short times, by loading MAP into a swellable insoluble polymer by any of the three proposed techniques. It is particularly interesting to observe that at five minutes MAP concentrations dissolved from the polymeric systems are even 10-100 times higher than from crystalline MAP.

3. "Continuous Flow" Dissolution Data

The "Continuous Flow" dissolution tablets of the MAP/swellable polymer systems was measured by placing the tablets in a thermostated beaker, containing 150 ml of pH 5.5 phosphate buffer solution at 37° C., magnetically stirred. The sample solution was continuously pumped via a perystaltic pump, Watson-Marlow, England, through a Sartorius membrane, to a spectrophotometer cell (SP-8-100, Pye Unicam), and then pumped back into the dissolution beaker. Concentrations of MAP were also checked by HPLC. The dissolution rates registered in "sink" conditions, i.e. up to MAP concentrations not higher than 20% of MAP solubility, are reported in Table III. The dissolution rates of the MAP/swellable polymer systems are very much higher than those of the commercial tablet and of the mixture of ground crystalline MAP and ground cross-linked PVP. These results stress the relevance of MAP loading on and in swellable polymers induced by any of the three preparation methods (grinding, heating, solvent swelling) described in this specification.

BIOAVAILABILITY OF MAP/SWELLABLE POLYMERS SYSTEMS

The bioavailability of MAP from the MAP/swellable polymer systems of this invention and prepared by the procedures described in the previous paragraphs has been checked and compared with that of MAP from a commercial formulation and from a physical mixture consisting of MAP and cross-linked PVP.

To this aim the above mentioned formulations have been administered (oral route, cross-over design) to 6 beagle dogs (male and female, 9-13 kg weight) not fed for 17 hours before and for 4 hours after treatment. At predetermined times after administration, 4 ml blood samples were taken, transferred into heparinized tubes and centrifuged (3,000 r.p.m., 10 min.). The separated plasma was stored frozen ($-20°$ C.) until analysis.

The MAP plasma levels were determined by a specific, accurate and precise method which consists of: (a) extraction of MAP with n-hexane, (b) clean-up of the extract (partition with acetonitrile), (c) high performance liquid chromatographic separation (column: Lichrosorb RP 18 Merck, mobile phase=methanol: water (75:25 v/v), flow rate 1 ml/min) and (d) UV (242 nm) detection. In a first study, dogs were treated (oral route, cross-over design) with 250 mg of MAP in a commercial formulation and with cross-linked PVP loaded with MAP (50 mg) by the cogrinding, solvent swelling and heating methods respectively. The data obtained and reported in Table IV show that MAP plasma levels after administration of the MAP/cross-linked PVP are comparable with or even higher than those produced by commercial tablets at a dose five times higher. Also the AUC values (7 hours) confirm the high)y enhanced bioavailability of MAP from the MAP/cross-linked PVP systems prepared by different procedures compared to that of MAP from a commercial formulation.

In a second study, dogs were treated (oral route, cross-over design) with tablets prepared using a physical mixture (1:3 w/w) of MAP (50 mg) and cross-linked PVP separately ground (3 hours) and with tablets prepared using a system consisting of MAP loaded (by cogrinding for 3 hours of 1:3 w/w mixture) in and on cross-linked PVP. The data obtained and reported in Table V show that oral treatment with MAP/cross-linked PVP system brings about a remarkable increase of plasma levels and AUC (7 hours) compared with those after oral administration of the physical mixture of MAP and cross-linked PVP.

From these findings and from the in vitro studies previously reported, it is possible to conclude that the MAP-swellable polymer systems described in this specification process the property to increase the dissolution characteristics of MAP and to enhance its bioavailability.

TABLE I

Differential Scanning Calorimetry Data of Various MAP/Swellable Polymer Systems.

| MAP preparation | Melting Point °C. | Heat of Fusion J/g | % Residual of Original Heat of Fusion |
|---|---|---|---|
| Pure crystalline MAP | 205-206 | 88.003 | 100% |
| Micronized pure MAP (3 hours of grinding) | 205.3 | 82.798 | 94.1% |
| MAP/cross-linked PVP 1:3 system (grinding method) Example 1 | 195.9 | 33.1 | 37.7% |
| MAP/Sodium Carboxymethylcellulose-cross-linked 1:5 system (grinding method) Example 4 | 204.4 | 44.6 | 50.6% |
| MAP/cross-linked PVP 1:5 system (heating method) Example 5 | — | ~0 | ~0% |
| MAP/cross-linked PVP 1:5 system (solvent swelling method) Example 7 | 195.2 | 85.4 | 97.1% |

TABLE II

Solubility Data (mcg/ml) of Various MAP/Swellable Polymer Systems (pH 5.5 phosphate buffer solution, at 37° C.).

| MAP preparation | 5 min | 15 min | 1 hr | 6 hrs |
|---|---|---|---|---|
| Pure crystalline MAP | <0.04 | 0.32 | 0.68 | 1.00 |
| MAP/cross-linked PVP 1:3 system (grinding method) Example 1 | 2.26 | 3.08 | 2.90 | 5.28 |
| MAP/cross-linked PVP 1:5 system (heating method) Example 5 | 3.83 | 6.10 | 4.76 | 3.28 |

TABLE II-continued

Solubility Data (mcg/ml) of Various MAP/
Swellable Polymer Systems
(pH 5.5 phosphate buffer solution, at 37° C.).

| MAP preparation | Time | | | |
|---|---|---|---|---|
| | 5 min | 15 min | 1 hr | 6 hrs |
| MAP/cross-linked PVP 1:5 system (solvent swelling method) Example 7 | 1.00 | 1.61 | 1.69 | 2.04 |

TABLE III

Dissolution Rate in "Sink" Conditions of Various MAP/Swellable Polymer Systems (continuous flow method, pH 5.5 phosphate buffer, at 37° C.).

| MAP preparation | Dissolution Rate mg/min |
|---|---|
| Commercial Tablet[a] (containing 250 mg crystalline MAP) | 0.144 |
| 1:3 w/w Physical Mixture[b] of ground crystalline MAP and ground cross-linked PVP (3 hrs of grinding) | 0.041 |
| 1:3 w/w MAP/cross-linked PVP System[b], prepared by grinding for 3 hrs (preparation of Example 2) | 0.428 |
| 1:5 w/w MAP/cross-linked PVP System[b], prepared by heating (preparation of Example 6) | 0.500 |
| 1:5 w/w MAP/cross-linked PVP System[b], prepared by solvent swelling (preparation of Example 8) | 0.530 |

[a]The commercial tablet unitary composition was: 250 mg of crystalline MAP; 121.25 mg of lactose, 60.00 mg of Corn Starch, 22.50 mg of linear polyvinylpyrrolidone, 31.25 mg of Sodium carboxymethyl starch, 5 mg of magnesium stearate.
[b]System containing 50 mg of MAP.

TABLE IV

Plasma MAP Concentrations (ng/ml) Determined by HPLC Method from Bioavailability Studies in Fasted Beagle Dogs (Means values and standard errors relative to six dogs)

| | Preparation | | | |
|---|---|---|---|---|
| Time (hrs) | Commercial[a] Tablet 1 × 250 mg | MAP/cross-linked PVP[b] 1:5 w/w System (heating method) 1 × 50 mg | MAP/cross-linked PVP[c] 1:5 w/w System (solvent swelling method) 1 × 50 mg | MAP/cross-linked PVP[d] 1:3 w/w System (cogrinding method) 1 × 50 mg |
| 1 | 12.94 (2.80) | 19.16 (6.35) | 23.48 (5.50) | 94.65 (39.56) |
| 2 | 20.33 (7.49) | 14.00 (2.52) | 41.38 (13.62) | 69.21 (19.93) |
| 4 | 26.73 (18.48) | 10.72 (1.95) | 16.06 (4.87) | 34.96 (15.45) |
| 7 | 9.51 (2.94) | 8.74 (3.74) | 8.52 (2.51) | 11.63 (2.73 |
| AUC[e] (0-7 hrs) mcg × hr/ml | 124.5 (48.1) | 80.07 (9.42) | 138.50 (32.30) | 303.31 (83.52) |

[a]Commercial tablet unitary composition was as follows: 250 mg of crystalline MAP; 121.25 mg of lactose; 60.00 mg of corn starch; 22.50 mg of linear polyvinylpyrrolidone; 31.25 mg of sodium carboxymethyl starch; 5 mg of magnesium stearate.
[b]Tablets were prepared as shown in Example 6.
[c]Tablets were prepared as shown in Example 8.
[d]Tablets were prepared as shown in Example 2.
[e]Area under the plasma MAP concentration-time curve.

TABLE V

Plasma MAP Concentrations (ng/ml) Determined by HPLC Method from Bioavailability Studies in Fasted Beagle Dogs. (Mean values and standard errors).

| | Preparation | |
|---|---|---|
| Time (hours) | Control Tablet[a] (Physical Mixture 1:3 w/w ground MAP ground cross-linked PVP) Mean of five dogs 2 × 50 mg | MAP cross-linked PVP[b] 1:3 w/w (by cogrinding) Mean of six dogs 2 × 50 mg |
| 1 | 9.71 (3.91) | 86.67 (41.81) |
| 2 | 13.24 (6.62) | 95.99 (29.41) |
| 4 | 31.19 (14.30) | 79.58 (44.58) |
| 7 | 11.01 (2.80) | 25.41 (9.10) |
| AUC[c] (0-7 hrs) mcg × hr/ml | 123.57 (35.45) | 467.7 (150.11) |

[a]Control tablets unitary composition was as follows: 200 mg of physical mixture 1:3 w/w of MAP and cross-linked PVP ground separately for 3 hours, 40 mg of cross-linked PVP alone as disintegrant. Each dog was given two tablets each containing 50 mg of MAP.
[b]Tablets of MAP cross-linked PVP system were prepared as shown in Example 2. Each dog was given two tablets each containing 50 mg of MAP.
[c]Area under the plasma MAP concentration-time curve.

Having now fully described this invention, it will be apparent to one of ordinary skill in the art that many changes and modifications can be made thereto without departing from the spirit or scope of the invention as set forth herein.

What is claimed as new and is intended to be secured by letters patent is:

1. A process for loading a water-swellable, water-insoluble polymer with methylhydroxyprogesterone acetate, which process comprises:
   preparing and grinding a mixture of said polymer and methylhydroxyprogesterone acetate.

2. A process for loading a water-swellable, water-insoluble polymer with methylhydroxyprogesterone acetate, which process comprises:
   (a) preparing a mixture of said polymer which is stable under the heating to which the mixture is subjected in step (b) and methylhydroxyprogesterone acetate; and
   (b) heating the mixture up to the melting temperature of methylhydroxyprogesterone acetate.

3. A process for loading a water-swellable, water-insoluble polymer with methylhydroxyprogesterone acetate, which process comprises:
   (a) swelling said polymer with a methylhydroxyprogesterone acetate solution which swells said polymer; and
   (b) drying the resulting swollen polymermethylhydroxyprogesterone acetate system.

4. The process according to claim 1, 2 or 3, wherein the weight ratio of MAP:swellable polymer is from 1:0.1 to 1:100 w/w.

5. The process according to claim 1, 2 or 3 wherein at least two water-insoluble polymers capable of being swelled by water are employed.

6. The process according to claim 1, 2 or 3, wherein the swellable, water-insoluble polymer is cross-linked polyvinylpyrrolidone.

7. The process according to claim 1, 2 or 3, wherein the swellable, water-insoluble polymer is cross-linked sodium carboxymethylcellulose.

8. A pharmaceutical composition comprising a water-swellable, water-insoluble polymer loaded with the methylhydroxyprogesterone formulation prepared as described in claim 1, 2 or 3.

9. The pharmaceutical composition according to claim 8, further comprising a pharmaceutically acceptable excipient.

10. A water-swellable, water-insoluble polymer loaded with MAP prepared by the process of claim 1, 2 or 3.

11. A water-swellable, water-insoluble polymer loaded with MAP prepared by a process comprising:
   (a) mixing MAP and cross-linked PVP in a mixer;
   (b) grinding the mixture;
   (c) sieving the ground mixture to eliminate aggregates; and
   (d) mixing the sieved material to ensure homogeneity of the mixture.

12. A water-swellable, water-insoluble polymer loaded with MAP prepared by a process comprising:
   (a) mixing MAP and cross-linked sodium carboxymethylcellulose in a mixer;
   (b) grinding the mixture;
   (c) sieving the ground mixture to eliminate aggregates; and
   (d) mixing the sieved material to ensure homogeneity of the mixture for the preparation of a dosage form.

13. A water-swellable, water-insoluble polymer loaded with MAP prepared by a process, comprising:
   (a) mixing MAP and cross-linked PVP in a mixer;
   (b) rotatively heating the mixture in a confining vessel within an oil bath at 215° C. for 45 minutes under an inert atmosphere;
   (c) sieving the heated mass to eliminate aggregates; and
   (d) mixing the sieved material to ensure homogeneity of the mixture for the preparation of a dosage form.

14. A water-swellable, water-insoluble polymer loaded with MAP prepared by a process comprising:
   (a) dissolving MAP in methylenechloride;
   (b) pouring the solution of step (a) over cross-linked PVP with gentle mixing of the materials;
   (c) drying the material obtained from step (b) at 60° C. for 2 hours;
   (d) sieving the resulting dried powdery material to eliminate aggregates; and
   (e) mixing the sieved material to ensure homogeneity of the mixture.

* * * * *

UNITED STATES PATENT AND TRADEMARK OFFICE
CERTIFICATE OF CORRECTION

PATENT NO. : 4,632,828

DATED : DECEMBER 30, 1986

INVENTOR(S) : FABIO CARLI

It is certified that error appears in the above-identified patent and that said Letters Patent is hereby corrected as shown below:

Column 1, line 27, delete "unfavourable" and insert --unfavorable--;

Column 1, line 60, delete "waterswellable" and insert --water-swellable--;

Column 2, line 60 delete "live" and insert --five--;

Column 3, line 37, delete "DSC" and insert --D.S.C.--. This term should be abbreviated as --D.S.C.-- in all instances throughout the patent.

Column 4, line 23, delete "compostions" and insert --compositions--;

Column 4, line 53, delete "evaporater" and insert --evaporator--.

Column 6, line 22, delete "were" and insert --was--;

line 45, delete "MAPSWELLABLE" and insert --MAP/SWELLABLE--; also "MAP-swellable" should be --MAP/swellable-- in all instances throughout the patent.

Column 7, line 30, delete "SP-8-100" and insert --SP8-100--.

UNITED STATES PATENT AND TRADEMARK OFFICE
CERTIFICATE OF CORRECTION

PATENT NO. : 4,632,828

DATED : DECEMBER 30, 1986

INVENTOR(S) : FABIO CARLI

It is certified that error appears in the above-identified patent and that said Letters Patent is hereby corrected as shown below:

Column 7, line 45, delete "POLYMERS" and insert --POLYMER--

Column 7, line 52, delete "above mentioned" and insert --above-mentioned--.

Column 8, line 9, delete "hig)ly" and insert --highly--;

line 43, delete "Example 1)" and insert --Example 1--.

Column 10, Table IV, delete "(2.73" and insert --(2.73)--.

Column 10, line 67, delete "polymermethylhy-" and insert --polymer-methylhy--.

Column 7, line 28, delete "perstaltic" and insert --peristaltic--.

Column 9, Table IV in the heading delete "Means" and insert --Mean--.

UNITED STATES PATENT AND TRADEMARK OFFICE
CERTIFICATE OF CORRECTION

PATENT NO. : 4,632,828

DATED : DECEMBER 30, 1986

INVENTOR(S) : FABIO CARLI

It is certified that error appears in the above-identified patent and that said Letters Patent is hereby corrected as shown below:

Throughout the patent carboxy-methylcellulose should be hyphenated in all instances.

Column 8, line 28, delete "process" and insert --possess--.

Signed and Sealed this

Nineteenth Day of April, 1988

Attest:

DONALD J. QUIGG

*Attesting Officer*  *Commissioner of Patents and Trademarks*